(12) United States Patent
Shrawat et al.

(10) Patent No.: US 9,217,001 B2
(45) Date of Patent: Dec. 22, 2015

(54) CRYSTALLINE BORTEZOMIB PROCESS

(71) Applicants: Vimal Kumar Shrawat, Raichur (IN); Rafiuddin, Raichur (IN); Vinod Kumar Singh, Raichur (IN); Akshay Kant Chaturvedi, Raichur (IN)

(72) Inventors: Vimal Kumar Shrawat, Raichur (IN); Rafiuddin, Raichur (IN); Vinod Kumar Singh, Raichur (IN); Akshay Kant Chaturvedi, Raichur (IN)

(73) Assignee: SHILPA MEDICARE LIMITED, Rajendra Gunj, Raichur, Karnataka (IN)

( * ) Notice: Subject to any disclaimer, the term of this patent is extended or adjusted under 35 U.S.C. 154(b) by 0 days.

(21) Appl. No.: 14/434,105

(22) PCT Filed: Nov. 12, 2013

(86) PCT No.: PCT/IN2013/000694
§ 371 (c)(1),
(2) Date: Apr. 8, 2015

(87) PCT Pub. No.: WO2014/076713
PCT Pub. Date: May 22, 2014

(65) Prior Publication Data
US 2015/0259364 A1 Sep. 17, 2015

(30) Foreign Application Priority Data
Nov. 16, 2012 (IN) .......................... 4780/CHE/2012

(51) Int. Cl.
*C07D 241/12* (2006.01)
*C07F 5/02* (2006.01)
*C07F 5/04* (2006.01)

(52) U.S. Cl.
CPC .............. *C07F 5/025* (2013.01); *C07D 241/12* (2013.01); *C07B 2200/13* (2013.01)

(58) Field of Classification Search
CPC ..................... C07F 5/025; C07B 2200/13
USPC ........................................................ 544/229
See application file for complete search history.

(56) References Cited

U.S. PATENT DOCUMENTS

| 4,525,309 A | 6/1985 | Matteson et al. |
| 5,780,454 A | 7/1998 | Adams et al. |
| 6,713,446 B2 | 3/2004 | Gupta |
| 7,714,159 B2 | 5/2010 | Pickersgill et al. |
| 2010/0226597 A1 | 9/2010 | Palle et al. |

FOREIGN PATENT DOCUMENTS

WO    2008075376 A1    6/2008

*Primary Examiner* — Venkataraman Balasubramanian

(57) ABSTRACT

The present invention provides process for preparation of crystalline Bortezomib (Ia) as its monohydrate which is designated as crystalline Form-SB

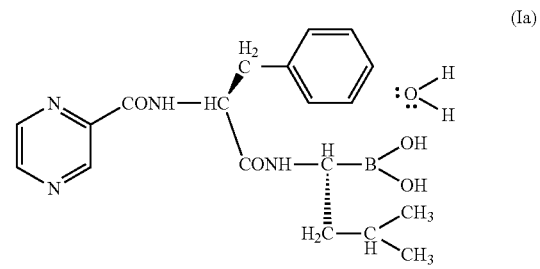

and characterized by having water content ranging between 3.5-6.0% w/w; X-ray powder diffraction pattern comprising characteristic 2θ° peaks selected from the XRPD peak set of 5.6, 7.5, 9.8, 10.2, 11.3, 15.1, 18.0, 20.5, 21.5 and 23.6±0.20 2θ°, wherein peaks at 9.8 and 11.39±0.20 2θ° are un-split and 100% intensity peak is present at 5.6±0.20 2θ°, DSC isotherm comprising the endothermic peaks ranging between 45 to 60° C. (Peak-1) and 175 to 185° C. (Peak-2) and IR absorption characteristic peaks approximately at 3387 $cm^{-1}$, 3304 $cm^{-1}$, 2953 $cm^{-1}$, 2927 $cm^{-1}$, 2868 $cm^{-1}$, 1627 $cm^{-1}$, 1455 $cm^{-1}$, 1400 $cm^{-1}$, 1201 $cm^{-1}$, 1150 $cm^{-1}$, 1020 $cm^{-1}$, 747 $cm^{-1}$ and 702 $cm^{-1}$ and Raman absorption spectra having characteristic peaks approximately at 3066 $cm^{-1}$, 1583 $cm^{-1}$, 1528 $cm^{-1}$, 1281 $cm^{-1}$, 1213 $cm^{-1}$, 1035 $cm^{-1}$, 1022 $cm^{-1}$ and 1004 $cm^{-1}$. The invention also provides the use of said crystalline Form-SB as active pharmaceutical ingredient in pharmaceutical compositions for the treatment of cancer.

10 Claims, 4 Drawing Sheets

CRYSTALLINE BORTEZOMIB PROCESS

INTRODUCTION

Bortezomib (I) is chemically known as [(1R)-3-methyl-1-[[(2S)-1-oxo-3-phenyl-2-[(pyrazinylcarbonyl)amino]propyl]amino]butyl]boronic acid and is represented by the structural Formula I

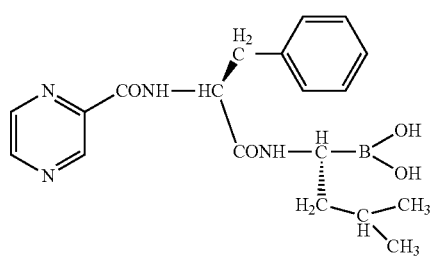

(I)

Bortezomib is a modified di-peptidyl boronic acid and can be represented as an N-protected dipeptide and may be written as Pyz-Phe-boro-Leu, which stands for pyrazinoic acid, phenylalanine and Leucine having a boronic acid group in place of carboxylic acid. It is a proteosome inhibitor in organisms and is believed to function as a reversible inhibitor of the chymotrypsin-like activity of the 26S proteasome in mammalian cells. The 26S proteasome is a large protein complex that degrades ubiquitinated proteins. The ubiquitin-proteasome pathway plays a role in regulating the intracellular concentration of specific proteins, maintaining homeostasis within cells. Inhibition of the 26S proteasome prevents this targeted proteolysis, which can affect multiple signaling cascades within the cell. This disruption of normal homeostatic mechanisms can lead to cell death.

Bortezomib is cytotoxic to a variety of cancer cell types in vitro and causes a delay in tumor growth in vivo in nonclinical tumor models, including multiple myeloma. Bortezomib presently is approved in USA for the treatment of multiple myeloma, relapsed multiple myeloma, and mantle cell lymphoma. A variety of combination therapies have been investigated for treating multiple myeloma, in which Bortezomib is administered with one or more other biologically active substances, such as lenalidomide, dexamethasone, melphalan, predisone, thalidomide, cyclophosphamide, doxorubicin, vincristine, carmustine, pomalidomide, vorinostat, tanespimycin, and perifosine. Other potential uses of Bortezomib also have been reported, including treatment of amyloidosis.

It is available in the market under the brand name "VELCADE™" in the form of injection. Each vial contains 3.5 mg of Bortezomib as a sterile lyophilized powder. Chemistry review section of Summary Basis of Approval for Bortezomib (NDA 21-602) mentions that the drug substance, drug product and the reconstituted drug product have three different molecular forms. PS-341 (Bortezomib) drug substance exists as the trimeric boroxine in the solid state. When exposed to water, the boroxine hydrolyses to monomeric boronic acid PS-341. The structure of the lyophilized PS-341 drug product has been determined to be symmetrical mannitol ester. While reconstituted by 0.9% NaCl solution, the reconstituted PS-341 drug product consists of equilibrium between the mannitol ester and the PS-341 boronic acid.

Adams et al in U.S. Pat. No. 5,780,454 disclosed Bortezomib, its pharmaceutically acceptable salts, pharmaceutical composition and use in inhibiting the proteosome function in a mammal. Further, it discloses a process for the preparation of Bortezomib and its analogues.

Gupta et al in U.S. Pat. No. 6,713,446 disclosed lyophilized formulation of Bortezomib esters. This patent mentions that Bortezomib prepared by the process as described in U.S. Pat. No. 5,780,454 is white amorphous powder.

U.S. Pat. No. 4,525,309 disclosed a process for the homologation of boronic esters by rearrangement of the intermediate boron "ate" complex in the presence of a Lewis acid catalyst to promote the rearrangement reaction and to minimize epimerization of α-carbon atom.

Pickersgill et al in U.S. Pat. No. 7,714,159 disclose processes for preparing Bortezomib and its intermediates which are boronic ester compounds. US '159 discloses that the previously reported processes for the preparation of the intermediate compound of the formula-III

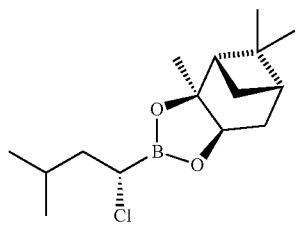

III by Lewis acid promoted rearrangement of boron "ate" complex of the formula —X

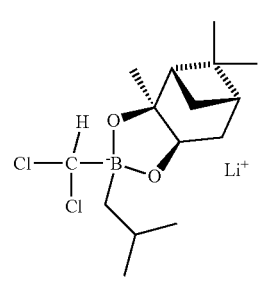

X employ tetrahydrofuran, an ether solvent that is miscible with water, and requires rigorously dried equipment, solvents, and Lewis acid reagent and such reactions are expensive and difficult to scale up. Further, according to the '159 patent, attempted scale-up of the prior art processes frequently results in further deterioration in diastereomeric ratio of the boronic ester compound either because of exposure of the product to halide ion during concentration of the reaction mixture to remove the tetrahydrofuran solvent and exchange it for a water-immiscible solvent or failure to completely remove the tetrahydrofuran during the subsequent aqueous washes.

US '159 appears to address the problems of the prior art by carrying out the rearrangement of the boron "ate" complex in an ether solvent that has low miscibility with water and a coordinating co-solvent. Non-limiting examples of low water miscible ether solvents identified in the US '159 application for use in the process include tert-butyl methyl ether, tert-butyl ethyl ether, tert-amyl methyl ether, and isopropyl ether.

Further, the US '159 application discloses a process for the preparation of Bortezomib which comprises:

(i) Providing a biphasic mixture comprising the intermediate boronic ester compound of formula-IX,

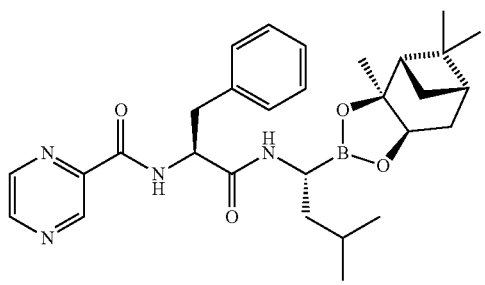

an organic boronic acid acceptor, a lower alkanol, a $C_{5-8}$ hydrocarbon solvent, and aqueous mineral acid;
(ii) stirring the biphasic mixture to afford Bortezomib;
(iii) separating the solvent layers; and
(iv) extracting Bortezomib or a boronic acid anhydride thereof into an organic solvent.

To enhance the purity of the product, the aqueous layer obtained after step (iii) is washed to remove neutral organic impurities prior to the extracting in step (iv). Such process comprises the following steps:
1) separating the solvent layers;
2) adjusting the aqueous layer to basic pH;
3) washing the aqueous layer with an organic solvent; and
4) adjusting the aqueous layer to a pH of less than about 6.

Thus, the process described in the US '159 comprises multiple organic solvent washings under acidic and basic conditions, followed by extracting the compound into an organic solvent, isolating the product and further recrystallization to obtain Bortezomib of enhanced purity.

It has been found that exposure of Bortezomib to an aqueous basic solution decrease the purity of Bortezomib. Particularly, when such process is performed on a large scale, exposure of Bortezomib to aqueous basic conditions for longer hours is difficult to avoid and hence this process may not be amenable for use on an industrial scale.

WO2008075376A1 discloses crystalline forms I and II of Bortezomib and process for their preparation. Form-I of Bortezomib is prepared by using solvents such as acetone, $CHCl_3$, $CH_2Cl_2$ or nitriles and diluents such as Diisopropyl ether, Tertiary butyl methyl ether, n-hexane and n-heptane. Form-II of Bortezomib is prepared from hot solution of ethyl acetate. The application also discloses that form-I and form-II are inter-changeable by using the above described solvents.

Palle et al in US2010/0226597 disclose a process for the preparation of Bortezomib, its intermediates and process for crystalline forms designated as Forms A and B of Bortezomib.

Bortezomib being an important anticancer therapeutic agent, additional and improved ways of preparing Bortezomib and its new solid crystalline form may be of immense value to pharmaceutical science and the healthcare of cancer patients. Hence, there exists a need in the development of new stable Bortezomib form and economically viable processes, which may be commercially up-scalable, viable, safer for handling, less time consuming and with better and consistent quality parameters.

The present inventors have found Bortezomib (Ia) as its stable crystalline monohydrate form designated as Form-SB and process for preparation thereof.

SUMMARY OF INVENTION

Particular aspects of the present application relates to the process/es for preparation of Crystalline Bortezomib (Ia).

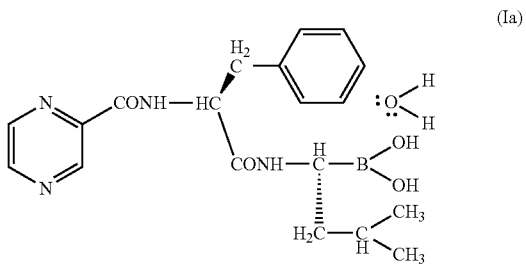

The application relates to process for preparation of Bortezomib (Ia) and its stable crystalline polymorphic form designated as Form-SB, which is substantially free from process related impurities. The crystalline polymorphic form of Bortezomib (Ia) obtained by the processes according to the present invention are useful as active pharmaceutical ingredient in pharmaceutical compositions for treatment of cancer particularly multiple myeloma, relapsed multiple myeloma, and mantle cell lymphoma, by administering the compound in a composition. Different aspects of the present application are summarized herein below individually.

In one aspect of the present application, it relates to Bortezomib monohydrate (Ia) crystalline

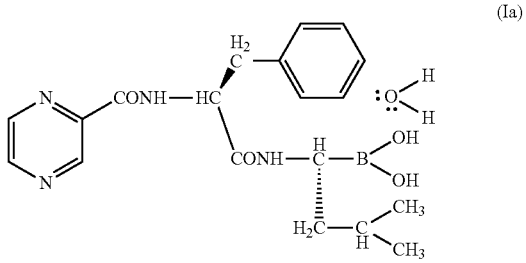

Form-SB characterized by having water content ranging between 3.5-6.0% w/w and X-ray powder diffraction pattern comprising characteristic 2θ° peaks selected from the XRPD peak set of 5.6, 7.5, 9.8, 10.2, 11.3, 15.1, 18.0, 20.5, 21.5 and 23.6±0.20 2θ°, wherein peaks at 9.8 and 11.39±0.20 2θ° are un-split and 100% intensity peak is present at 5.6±0.20 2θ°.

Said Bortezomib (Ia) Crystalline form-SB is further characterized by DSC isotherm comprising two endothermic peaks ranging between
 a. Peak-1—Between 45 to 60° C.
 b. Peak-2—Between 175-185° C.

Bortezomib (Ia) according to present invention has an IR absorption spectrum having characteristic peaks expressed in $cm^{-1}$ at approximately 3387 $cm^{-1}$, 3304 $cm^{-1}$, 2953 $cm^{-1}$, 2927 $cm^{-1}$, 2868 $cm^{-1}$, 1627 $cm^{-1}$, 1455 $cm^{-1}$, 1400 $cm^{-1}$, 1201 $cm^{-1}$, 1150 $cm^{-1}$, 1020 $cm^{-1}$, 747 $cm^{-1}$ and 702 $cm^{-1}$ and Raman absorption spectrum having characteristic peaks expressed in $cm^{-1}$ at approximately 3066 $cm^{-1}$, 1583 $cm^{-1}$, 1528 $cm^{-1}$, 1281 $cm^{-1}$, 1213 $cm^{-1}$, 1035 $cm^{-1}$, 1022 $cm^{-1}$ and 1004 $cm^{-1}$.

In another aspect of the present invention, Bortezomib (Ia) crystalline Form-SB is further characterized by X-ray powder diffraction pattern substantially according to FIG. 1, DSC isothermal pattern substantially according to FIG. 2, IR absorption spectrum substantially according to FIG. 3 and Raman spectrum substantially according to FIG. 4.

In yet another aspect of the present invention, it relates to a process for preparing Bortezomib (Ia) crystalline Form-SB characterized by X-ray powder diffraction pattern comprising the characteristic 2θ° peaks of 5.6, 7.5, 9.8, 10.2, 11.3, 15.1, 18.0, 20.5, 21.5 and 23.6±0.20 2θ°, wherein peaks at 9.8 and 11.39±0.20 2θ° are un-split and 100% intensity peak is present at 5.6±0.20 2θ°, DSC isotherm comprising the endothermic peaks ranging between 45 to 60° C. (Peak-1) and 175 to 185° C. (Peak-2) and IR absorption characteristic peaks approximately at 3387 cm$^{-1}$, 3304 cm$^{-1}$, 2953 cm$^{-1}$, 2927 cm$^{-1}$, 2868 cm$^{-1}$, 1627 cm$^{-1}$, 1455 cm$^{-1}$, 1400 cm$^{-1}$, 1201 cm$^{-1}$, 1150 cm$^{-1}$, 1020 cm$^{-1}$, 747 cm$^{-1}$ and 702 cm$^{-1}$ and Raman absorption having characteristic peaks at approximately 3066 cm$^{-1}$, 1583 cm$^{-1}$, 1528 cm$^{-1}$, 1281 cm$^{-1}$, 1213 cm$^{-1}$, 1035 cm$^{-1}$, 1022 cm$^{-1}$ and 1004 cm$^{-1}$, wherein the process comprise the steps of— a. Combining the bortezomib with an aliphatic ester (C3 to C8) solvent or a mixture of aliphatic ester (C3 to C8) solvent and water
b. raise the temperature up to about 40-70° C.
c. Stir the solution at same temperature up to a time between 15 to 60 minutes.
d. combine with aliphatic C6 to C7 hydrocarbon solvent
e. optionally maintain the mixture for 10-60 minutes
f. cooling the mixture up to about 10-40° C.
g. isolating the crystalline material Individual steps of the present invention are detailed in the further text of the specification with non-limiting examples represented in the relevant sections of the specification.

In a further aspect, the Crystalline Form SB of Bortezomib monohydrate (Ia) obtained by the process/es according to the present application may be formulated as compositions for injectable or oral administration in the form of powders, solutions, capsules, tablets, pills, or granules useful in the treatment of hyper-proliferative disorders, such as cancer. Further aspects of the present invention are demonstrated in detailed description section as well as examples.

DETAILED DESCRIPTION

Figure 1:
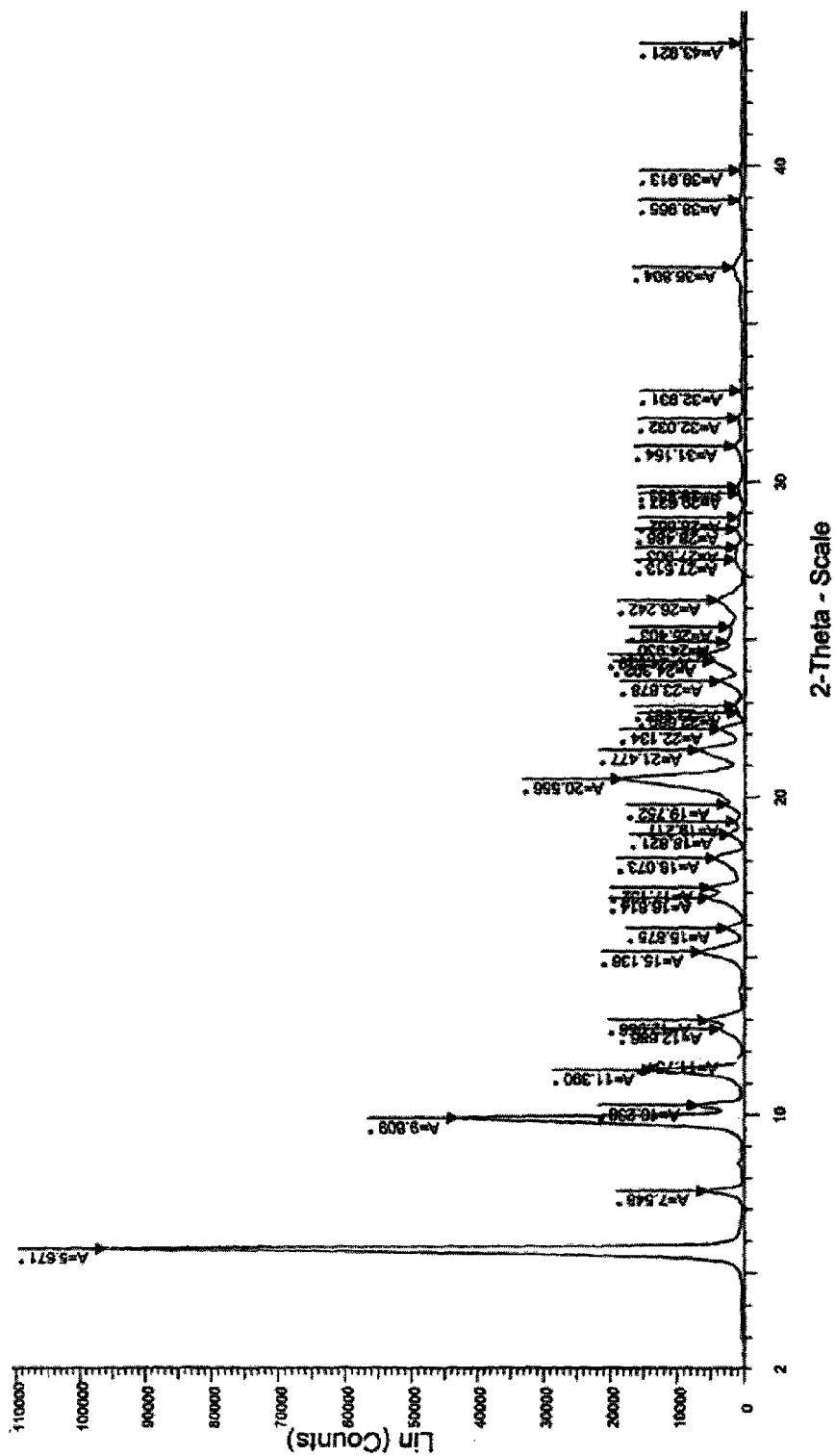
FIG. 1 is Illustration of X-ray powder diffraction (XRPD) pattern of Bortezomib monohydrate-Form SB, prepared according to Example-3

According to the embodiments of the present invention as set forth herein, the present invention provides crystalline polymorphic Form SB of Bortezomib monohydrate (Ia), processes for preparation thereof and pharmaceutical compositions of Form-SB useful in the treatment of hyper-proliferative disorders, such as cancer. Individual embodiments of the present invention are detailed herein below separately.

In one embodiment of the present application, it provides Bortezomib monohydrate (Ia) crystalline Form-SB,

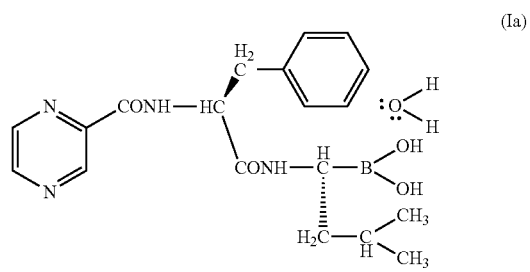

(Ia)

characterized by having water content ranging between 3.5-6.0% w/w and X-ray powder diffraction pattern comprising characteristic 2θ° peaks selected from the XRPD peak set 5.6, 7.5, 9.8, 10.2, 11.3, 15.1, 18.0, 20.5, 21.5 and 23.6±0.20 2θ°, wherein peaks at 9.8 and 11.39±0.20 2θ° are un-split and 100% intensity peak is present at 5.6±0.20 2θ°.

Said Bortezomib (Ia) Crystalline form-SB is further characterized by DSC isotherm comprising two endothermic peaks ranging between
a) Peak-1—Between 45 to 60° C.
b) Peak-2—Between 175-185° C.

The characteristic and main peaks and their d spacing values of the new crystalline Form-SB are tabulated in the Table-1.

TABLE 1

Characteristic XRPD Peaks of Crystalline Form-SB

| S. No. | Angle (2θ°) ± 0.20 | d Spacing Value (Å) |
|---|---|---|
| 1. | 5.67 | 15.570 |
| 2. | 7.55 | 11.702 |
| 3. | 9.81 | 9.010 |
| 4. | 10.24 | 8.633 |
| 5. | 11.39 | 7.763 |
| 6. | 12.96 | 6.828 |
| 7. | 15.14 | 5.849 |
| 8. | 16.81 | 5.269 |
| 9. | 18.07 | 4.90 |
| 10. | 20.56 | 4.317 |
| 11. | 21.48 | 4.134 |
| 12. | 23.68 | 3.755 |
| 13. | 24.53 | 3.626 |
| 14. | 26.24 | 3.393 |

A few minor variations in the observed 2θ° angle values may be expected based on the analyst person, the specific XRPD diffractometer employed and the sample preparation technique. Further possible variations may also be expected for the relative peak intensities, which may be largely affected by the non-uniformity of the particle size of the sample. Hence, identification of the exact crystalline form of a compound should be based primarily on observed 2 theta angles with lesser importance attributed to relative peak intensities. The 2 theta diffraction angles and corresponding d-spacing values account for positions of various peaks in the X-ray powder diffraction pattern. D-spacing values are calculated with observed 2 theta angles and copper Kα wavelength using the Bragg equation well known to those having skill in the art of XRPD diffractometry science.

In view of possibility of marginal error in the assigning 2 theta angles and d-spacing, the preferred method of comparing X-ray powder diffraction patterns in order to identify a particular crystalline form is to overlay the X-ray powder diffraction pattern of the unknown form over the X-ray powder diffraction pattern of a known form. For example, one skilled in the art can overlay an X-ray powder diffraction pattern of an unidentified crystalline form of Bortezomib over FIG. 1 and readily determine whether the X-ray diffraction pattern of the unidentified form is substantially the same as the X-ray powder diffraction pattern of the crystalline form of this invention. If the X-ray powder diffraction pattern is substantially the same as FIG. 1, the previously unknown crystalline form of Bortezomib can be readily and accurately identified as the crystalline Form-SB of this invention.

The crystalline Form-SB of Bortezomib appears to be monohydrate, which may be evident from the moisture determination resulting in water content in the range of 3.5-6.0% w/w. A sample of the crystalline Bortezomib-Form-SB prepared by the process according to the present invention had moisture content up to ~4.24% w/w, which has also confirmed the monohydrate nature of the compound. (Theoretically calculated moisture content value for the monohydrate Bortezomib is about 4.47% w/w). Inventors of the present application, during the process of their studies on moisture content determination in Bortezomib, observed that conventional Karl Fischer (KF) method for water determination often yields a false and higher water content value for Bortezomib owing to apparent reaction with KF reagent itself releasing variable additional amount of water. To overcome this analytical limitation in order to ascertain the actual water content, which may also be consistently reproducible, another process for determination of moisture content in Bortezomib was developed by the inventors of the present application. According to this method, the moisture content was determined by using KF Coulometric titration with KF Thermo prep. (Oven parameters—Temperature: 140° C., $N_2$ or air Gas Flow: 60 mL/Min). This coulometric method of moisture content determination consistently provides reliable moisture content results.

While the invention is not limited to any specific theory, it should be understood however that the crystalline form SB of Bortezomib monohydrate may contain additional residual or unbound moisture corresponding to slightly more than stoichiometric water content without losing its monohydrate character and/or its monohydrate crystalline form-SB characteristics. Nevertheless, person having skill in the art should be able to determine whether they are same crystalline forms or not, by looking at the overall shape of the X-ray powder diffraction pattern optionally with help of other thermal data like DSC or IR/Raman.

Further, Bortezomib crystalline form-SB according to present invention has IR absorption spectrum having characteristic peaks expressed in $cm^{-1}$ at approximately 3387 $cm^{-1}$, 3304 $cm^{-1}$, 2953 $cm^{-1}$, 2927 $cm^{-1}$, 2868 $cm^{-1}$, 1627 $cm^{-1}$, 1455 $cm^{-1}$, 1400 $cm^{-1}$, 1201 $cm^{-1}$, 1150 $cm^{-1}$, 1020 $cm^{-1}$, 747 $cm^{-1}$ and 702 $cm^{-1}$ and Raman absorption spectrum having characteristic peaks expressed in $cm^{-1}$ at approximately 3066 $cm^{-1}$, 1583 $cm^{-1}$, 1528 $cm^{-1}$, 1281 $cm^{-1}$, 1213 $cm^{-1}$, 1035 $cm^{-1}$, 1022 $cm^{-1}$ and 1004 $cm^{-1}$.

An in-depth review of the Raman spectra along with general literature for Boronic acid compounds provides that series of Raman absorption bands at 1213, 1245 and 1281 $cm^{-1}$ are apparently ascribed to OH groups of boronic acid in-plane bending modes. Further, multiple Raman bands in the OH stretching region are also observed at 3206 and 3249 $cm^{-1}$ leading to a belief about nature of the Crystalline Form-SB of [(1R)-3-methyl-1-({(2S)-3-phenyl-2-[(pyrazin-2-ylcarbonyl)amino]propanoyl}amino)butyl]boronic acid as monohydrate, which may be coordinated with electron lone pair/s residing on oxygen atom of water molecule.

Figure 2:
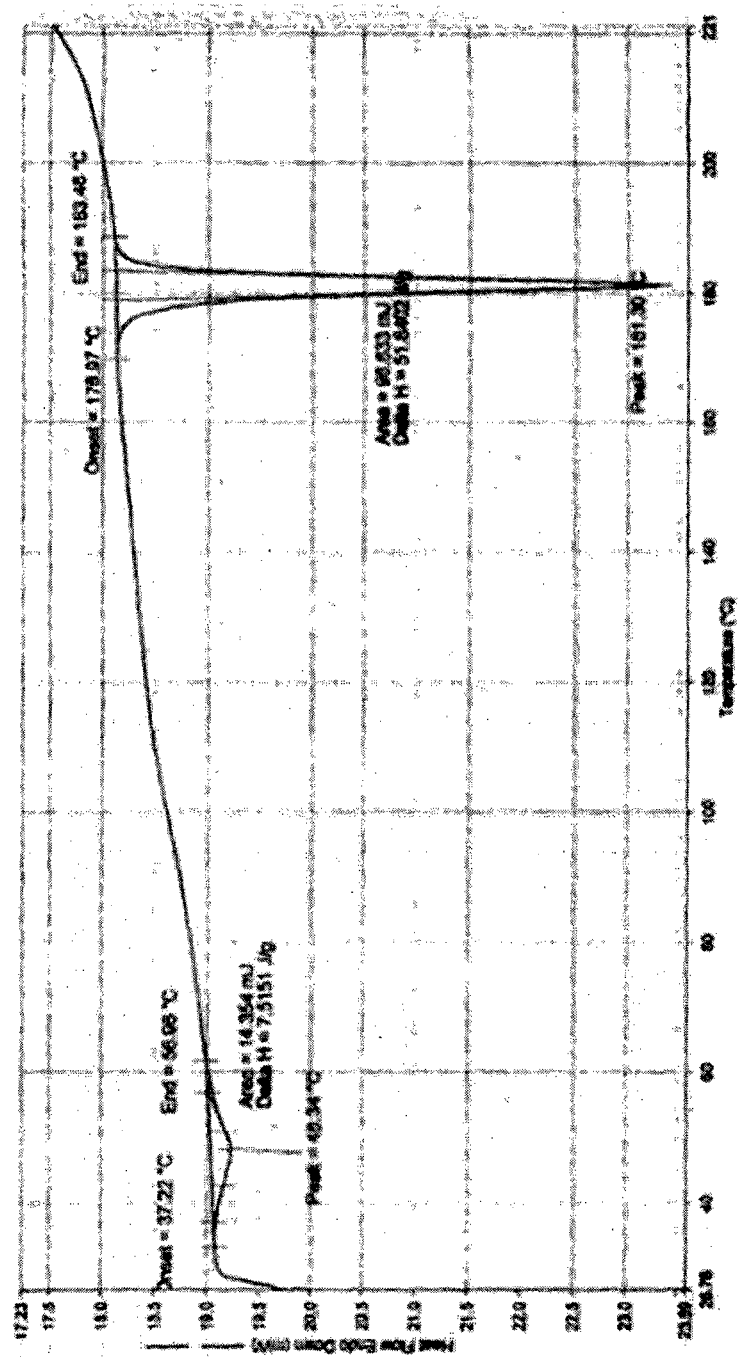
FIG. 2 is an Illustration of a differential scanning calorimetric ("DSC") curve of Bortezomib monohydrate-Form SB, prepared according to Example-3
Figure 3:
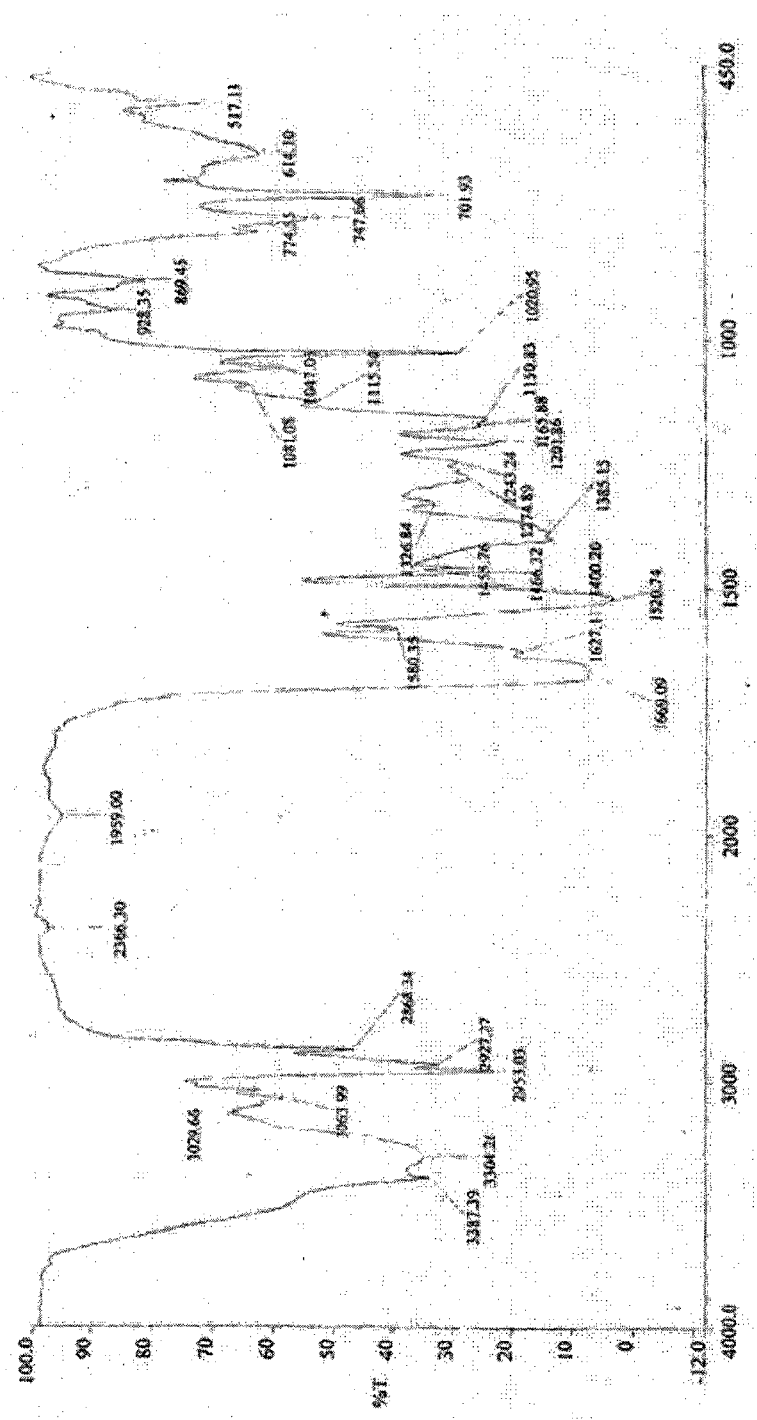
FIG. 3 is an Illustration of an IR spectrum of Bortezomib monohydrate-Form SB, prepared according to Example-3
Figure 4:
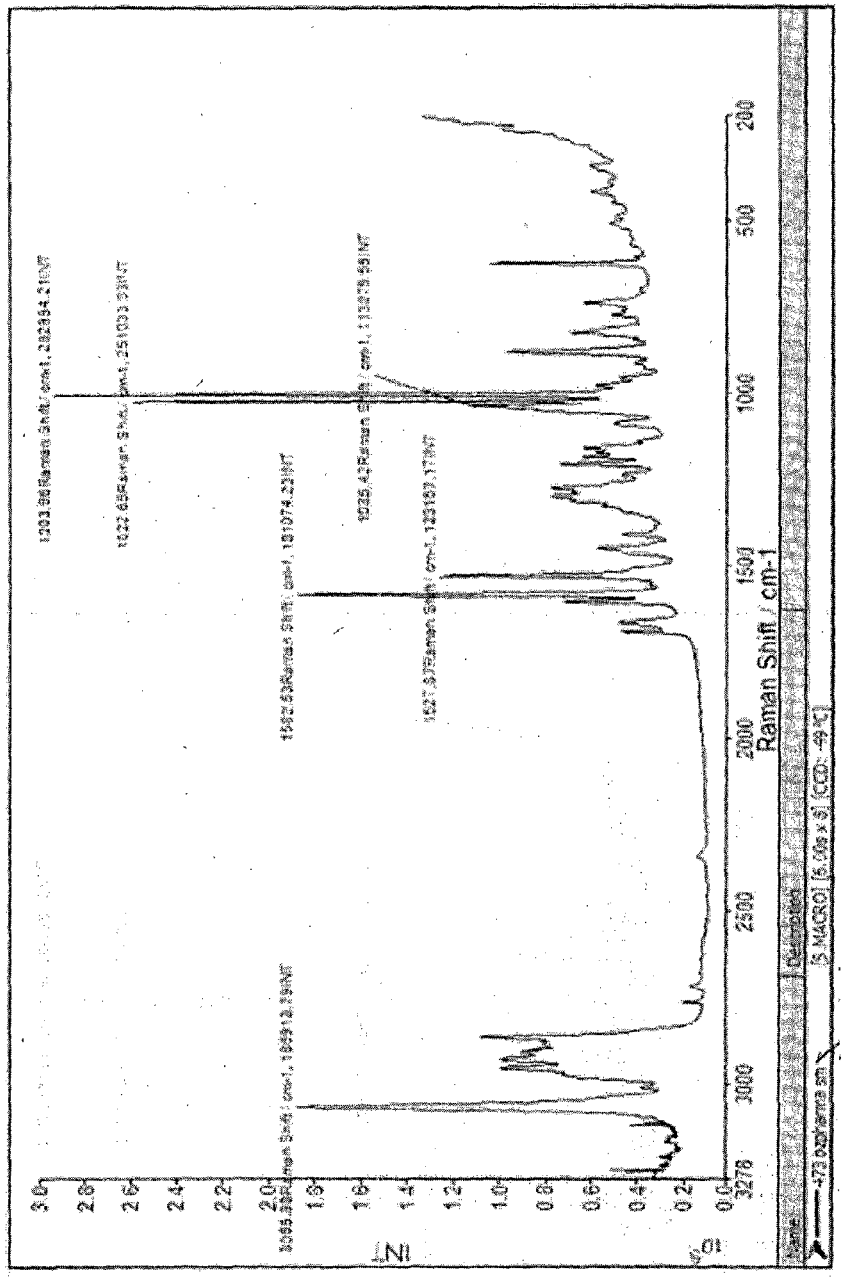
FIG. 4 is an Illustration of a Raman spectrum of Bortezomib monohydrate-Form SB, prepared according to Example-3

Embodiments of the present invention encompass Bortezomib (Ia) crystalline Form-SB, which is in particular characterized by X-ray powder diffraction pattern substantially according to FIG. 1, DSC isothermal pattern substantially according to FIG. 2, IR absorption spectrum substantially according to FIG. 3 and Raman spectrum substantially according to FIG. 4.

In further embodiment of the present invention, it provides process for preparing Bortezomib (Ia) crystalline Form-SB characterized by X-ray powder diffraction pattern comprising the characteristic 2θ° peaks of 5.6, 7.5, 9.8, 10.2, 11.3, 15.1, 18.0, 20.5, 21.5 and 23.6±0.20 2θ°, wherein peaks at 9.8 and 11.39 0.20 2θ° are un-split and 100% intensity peak is present at 5.6±0.20 2θ°, DSC isotherm comprising the endothermic peaks ranging between 45 to 60° C. (Peak-1) and 175 to 185° C. (Peak-2) and IR absorption characteristic peaks at approximately 3387 $cm^{-1}$, 3304 $cm^{-1}$, 2953 $cm^{-1}$, 2927 $cm^{-1}$, 2868 $cm^{-1}$, 1627 $cm^{-1}$, 1455 $cm^{-1}$, 1400 $cm^{-1}$, 1201 $cm^{-1}$, 1150 $cm^{-1}$, 1020 $cm^{-1}$, 747 $cm^{-1}$ and 702 $cm^{-1}$ and Raman absorption spectrum having characteristic peaks at approximately 3066 $cm^{-1}$, 1583 $cm^{-1}$, 1528 $cm^{-1}$, 1281 $cm^{-1}$, 1213 $cm^{-1}$, 1035 $cm^{-1}$, 1022 $cm^{-1}$ and 1004 $cm^{-1}$, comprising the steps of— a. Combining the Bortezomib with an aliphatic ester solvent or a mixture of aliphatic ester solvent and water b. raise the temperature up to about 40-70° C.

c. Stir the solution at same temperature up to a time between 15 to 60 minutes.

d. combine with aliphatic C6 to C7 hydrocarbon solvent e. optionally maintain the mixture for 10-60 minutes f. cooling the mixture up to about 10-40° C.

g. isolating the crystalline material.

Step of combining the Bortezomib with an aliphatic ester (C3 to C8) solvent or a mixture of aliphatic ester (C3 to C8) solvent and water comprise either mixing or suspending or making solution with Bortezomib obtained by any process/any form with an aliphatic ester (C3 to C8) solvent or a mixture of aliphatic ester (C3 to C8) solvent and water, having a water content in the range between 1-10% w/w. In a preferred embodiment, water content in a mixture of aliphatic ester (C3 to C8) solvent and water, ranges between 3-5%. In this embodiment, it may be understood that representing mixture of aliphatic ester solvent and water having ratio between 90:10 to 99:1 v/v means the same for the purpose of present invention. The temperature of combining the solvent and Bortezomib may range between 20-40 deg C.

In this embodiment, aliphatic ester (C3 to C8) solvent used may be selected from methyl acetate, ethyl acetate, propyl acetate or the like. In a particular embodiment, aliphatic ester as ethyl acetate was used for preparing Form-SB of Bortezomib. Any form of Crude or Pure Bortezomib obtained by known processes may be used for preparing Form-SB.

In an embodiment of the present invention, process represented in the Scheme-I was utilized to obtain the Bortezomib.

Scheme-I: Process for preparation of Bortezomib

R-Boroleu-(+)-pinanediol trifluoroacetic acid

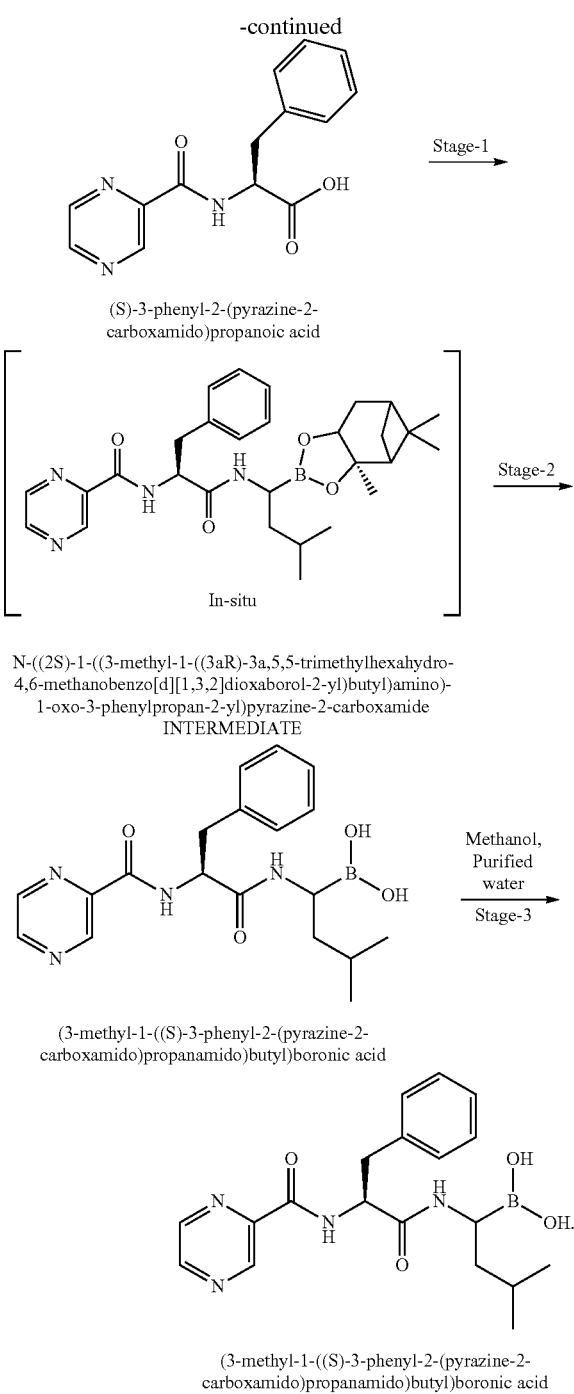

(S)-3-phenyl-2-(pyrazine-2-carboxamido)propanoic acid

Stage-1 →

N-((2S)-1-((3-methyl-1-((3aR)-3a,5,5-trimethylhexahydro-4,6-methanobenzo[d][1,3,2]dioxaborol-2-yl)butyl)amino)-1-oxo-3-phenylpropan-2-yl)pyrazine-2-carboxamide
INTERMEDIATE In-situ Stage-2 →

Methanol, Purified water
Stage-3 →

(3-methyl-1-((S)-3-phenyl-2-(pyrazine-2-carboxamido)propanamido)butyl)boronic acid (3-methyl-1-((S)-3-phenyl-2-(pyrazine-2-carboxamido)propanamido)butyl)boronic acid The specifics of the process are detailed and can be clearly understood by a person skilled in the art from the examples represented below in the example section. A material obtained by the process may directly be processed to the stage resulting in Crystalline Form-SB of the present invention.

In the step of raising the temperature in the range about 40-70° C., it is preferred to perform the heating gradually followed by continued stirring of the solution at same temperature up to a time ranging between 15 to 60 minutes. The step of combining aliphatic C6 to C7 hydrocarbon solvent is an important step, wherein crystalline form-SB gets isolated. The solution may optionally be maintained under stirring for a time ranging between 10-60 minutes in order to retain the maximum isolation of the crystalline material.

The step of cooling the mixture may be carried out for the mixture up to about 10-40° C. as per need to attain the crystalline material to be precipitated out with no or minimal possible degradation. Simultaneously, it is also essentially required to cool the solution in the successive lower rate of cooling in order to retain the characteristics of Form-SB, while achieving the pure crystal formation.

The process related impurities, including unreacted intermediates, side products, degradation products and other medium dependent impurities, that appears in the impurity profile of the Bortezomib monohydrate can substantially be removed by the process of the present invention resulting in the formation of crystalline Form-SB. A substantially pure product having purities more than 99.5% (by HPLC) can be obtained by the process of the present invention. In view of maintaining the equilibrium to the impurity profile compliance, the process requires frequent quality checks, while raising the temperature especially in step b) up to 40-70° C.

The product may be isolated from the reaction mass by conventional processes including filtering and optional drying, which may be carried out at room temperature for the suitable durations to retain the crystalline polymorphic form characteristics. Crystalline Form-SB can be recovered by conventional processes, which are not limited to scrapping, breaking, triturating and if required conventional drying.

Bortezomib monohydrate crystalline Form-SB obtained according to present invention shall be dried under vacuum; however, water content corresponding to monohydrate gets retained in the range between 3.5-6.0% w/w (including residual/channel water if any).

The Crystalline Form-SB of Bortezomib monohydrate described herein is characterized by X-ray powder diffraction pattern (XRPD) and IR absorption spectra and Thermal techniques such as differential scanning calorimetric (DSC) Analysis. The samples of Bortezomib monohydrate Crystalline Form-SB were analyzed by XRPD on a Bruker AXS D8 Advance Diffractometer using X-ray source—Cu Kα radiation using the wavelength 1.5418 Å and DSC analysis were carried out on a Perkin Elmer Jade instrument and RAMAN spectra was carried out on Perkin Elmer Raman Station 400 instrument. Illustrative examples of analytical data for the Crystalline Form-SB of Bortezomib monohydrate obtained in the Examples are set forth in the FIGS. 1-4.

In a further embodiments of the present invention, the Crystalline Form SB of Bortezomib monohydrate (Ia) obtained by the process/es according to the present application may be formulated as compositions for injectable or oral administration in the form of powders, solutions, capsules, tablets, pills, or granules useful in the treatment of hyperproliferative disorders, such as cancer.

Crystalline Form-SB of Bortezomib monohydrate of the present invention may have one or more advantageous and desirable properties compared to the known Bortezomib as anhydrate or trimeric form, which are not limited to better stability, solubility and quality parameter (improved purity; >99.5%) leading to improved shelve life, storage and distribution.

In Bortezomib monohydrate Crystalline Form-SB compositions, the active product is mixed with one or more pharmaceutically acceptable excipients. The drug substance can be formulated as lyophilized or ready to use compositions for injectable or solid/liquid compositions for oral administration including solutions, suspensions, syrups, elixirs and emulsions, containing solvents or vehicles such as water, sorbitol, glycerine, propylene glycol or liquid paraffin.

The compositions for parenteral administration can be solutions, suspensions, emulsions or aqueous or non-aqueous sterile solutions. As a solvent or vehicle, propylene glycol, polyethylene glycol, vegetable oils, especially olive oil, and injectable organic esters, e.g. ethyl oleate, may be employed.

These compositions can contain adjuvants, especially wetting, emulsifying and dispersing agents. The sterilization may be carried out in several ways, e.g. using a bacteriological filter, by incorporating sterilizing agents in the composition, by irradiation or by heating. They may be prepared in the form of sterile compositions, which can be dissolved at the time of use in sterile water or any other sterile injectable medium.

Pharmaceutically acceptable excipients used in the compositions comprising Crystalline Form-SB of Bortezomib monohydrate of the present application include, but are not limited to diluents such as starch, pregelatinized starch, lactose, powdered cellulose, microcrystalline cellulose, dicalcium phosphate, tricalcium phosphate, mannitol, sorbitol, sugar and the like; binders such as acacia, guar gum, tragacanth, gelatin, pre-gelatinized starch and the like; disintegrants such as starch, sodium starch glycolate, pregelatinized starch, Croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants, waxes and the like. Other pharmaceutically acceptable excipients that are of use include but not limited to film formers, plasticizers, colorants, flavoring agents, sweeteners, viscosity enhancers, preservatives, antioxidants and the like.

Pharmaceutically acceptable excipients used in the compositions derived from Crystalline Form-SB of Bortezomib monohydrate of the present application may also comprise to include the pharmaceutically acceptable carrier used for the preparation of solid dispersion, wherever utilized in the desired dosage form preparation.

Certain specific aspects and embodiments of the present application will be explained in more detail with reference to the following examples, which are provided by way of illustration only and should not be construed as limiting the scope of the invention in any manner.

EXPERIMENTAL DETAILS

The process for preparation according to the present invention of crystalline Bortezomib Form-SB may be demonstrated by examples as given below.

Example 1

Preparation of Bortezomib

Preparation of Bortezomib Comprise of Three Main Stages

Stage-1: Preparation of N-((2S)-1-((3-methyl-1-((3aR)-3a,5,5-trimethylhexahydro-4,6-methanobenzo[d][1,3,2]dioxaborol-2-yl)butyl)amino)-1-oxo-3-phenylpropan-2-yl)pyrazine-2-carboxamide (Intermediate, which is used without isolation for the next stage)

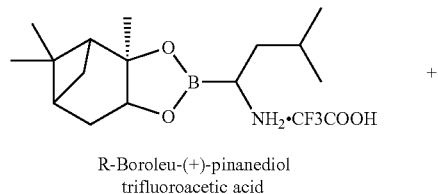

R-Boroleu-(+)-pinanediol trifluoroacetic acid

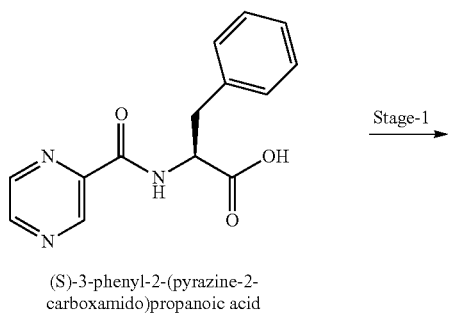

(S)-3-phenyl-2-(pyrazine-2-carboxamido)propanoic acid

Stage-1 →

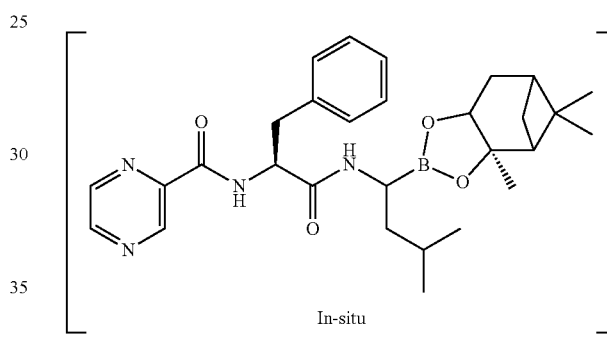

N-((2S)-1-((3-methyl-1-((3aR)-3a,5,5-trimethylhexahydro-4,6-methanobenzo[d][1,3,2]dioxaborol-2-yl)butyl)amino)-1-oxo-3-phenylpropan-2-yl)pyrazine-2-carboxamide
Intermediate, which is used without isolation for the next stage Take 98 ml MDC under nitrogen and add 7 gm of (S)-3-phenyl-2-(pyrazine-2carboxamido) propanoic acid, 3.3 gm of N-Hydroxy succinimide and 6.0 gm of N,N-Diyclohexyl-carbodiimide. Stir the reaction solution for 20 min at room temperature and under continuous $N_2$ purging.

Charge (R) Boroleu pinanediol trifluoro acetic acid 9.8 gm and 7.0 ml triethylamine and continue stirring for about 4 hrs at room temperature and under continuous $N_2$ purging. Filter the mass and wash the cake with 20 ml methylene dichloride (MDC). Collect MDC layer and wash with IN HCl 200 ml followed by 200 ml of saturated solution of sodium bicarbonate.

Dry the MDC layer with dried sodium sulphate. Distill out MDC under vacuum below 40 deg C and add 98 ml methanol and redistill. Again add 98 ml methanol and redistill under vacuum at 45 deg C to get Stage 1-Intermediate material as residue.

Stage 2: Converting Stage-1 residue in-situ into Crude Bortezomib i.e. ((3-methyl-1-((S)-3-phenyl-2 (pyrazine-2-carboxamido)propanamido)butyl)boronic acid

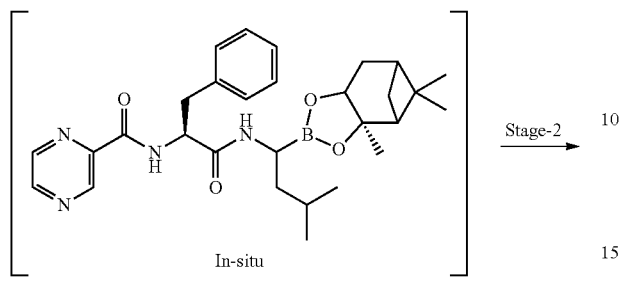

N-((2S)-1-((3-methyl-1-((3aR)-3a,5,5-trimethylhexahydro-4,6-methanobenzo[d][1,3,2]dioxaborol-2-yl)butyl)amino)-1-oxo-3-phenylpropan-2-yl)pyrazine-2-carboxamide
INTERMEDIATE-INSITU

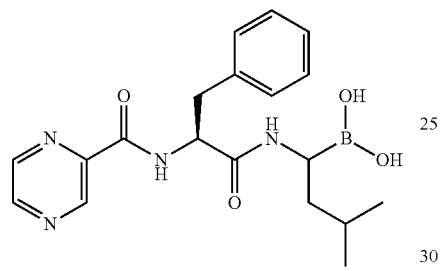

(3-methyl-1-((S)-3-phenyl-2-(pyrazine-2-carboxamido)propanamido)butyl)boronic acid Add 255 ml methanol to the stage I-Intermediates residue (In-situ material) and add about 255 ml n-Heptane at room temperature. Charge 3.0 gm iso-butyl boronic acid and 255 ml of freshly prepared 1 N HCl aq. solution. Stir the mass at room temperature (20-30 deg C) for about 90 min Separate n-Heptane Organic layer. Again charge 255 ml n-Heptane, stir for 60 min at RT and separate n-Heptane layer. Repeat the same process once again.

Distill off methanol from aq. layer until the mass is turbid under vacuum below 45 deg C. Cool the solution to RT and extract the product with 255 ml×3 times with MDC. Collect the MDC layers and wash the MDC layer with 128 ml of saturated solution of sodium bicarbonate, followed by 128 ml of brine solution. Dry the said MDC layer with sodium sulphate and distill off MDC completely under vacuum at below 45 deg C. Add 128 ml×2 times ethyl acetate and distill out under vacuum below 45 deg C. Charge 25 ml ethyl acetate at 45 deg C and slowly cool the solution to about 20-25 deg C.

Start adding slowly up to about 95 ml toluene and continue stirring for about 2 hrs at RT for material crystallization. Filter the mass by suck drying, wash the material with 128 ml of 5% ethyl acetate in toluene followed by drying at RT under vacuum.
Yield=4.2 gm
Purity=98.8% (by HPLC)

Stage 3: Preparing pure ((3-methyl-1-((S)-3-phenyl-2-(pyrazine-2-carboxamido)propanamido)butyl) boronic acid monohydrate 1) Charge 12 ml methanol at RT in a RB flask and add Stage 2 material (4.0 gm) at RT.
2) Stir the solution at RT for complete dissolution.
3) Charge 12 ml water slowly in about 30-60 min and stir for 2 hrs at RT.
4) Filter the mass and wash with 6 ml methanol+6 ml water mixture followed by suck drying and unloading.
5) Dry the unloaded material at 40-45 deg C under vacuum.
Dry wt. (Yield)=3.5 gm.
Purity=99.65% (By HPLC)

Example 2

Preparation of Crystalline Bortezomib monohydrate (Form-SB)

3.5 gm Stage 3 material (of example 1) is dissolved in 87.5 volumes of ethyl acetate at 40 deg to 45 deg C and filtered. Start addition of 87.5 ml n-Heptane slowly at 40-45 deg C. Slowly cool the solution mass to 25-30 deg C. Stop stirring and maintain for about 4 hrs. Filter and dry under vacuum at 40 deg C to get Bortezomib.
Dry wt. (Yield=3.0-3.2 gm)
Purity=99.7% (By HPLC)

Example 3

Preparation of Crystalline Bortezomib monohydrate (Form-SB)

a) In a clean RB flask, 50 ml mixture of ethyl acetate: water (95:5) is charged.
b) Add 2.0 gm Bortezomib-Pharma and stir the solution for 10-15 minutes at 25-30° C.
c) Slowly raise the temperature of the mixture to 40-45° C. to get the clear solution.
d) Filter the clear solution obtained in the above step through membrane paper.
e) Into the clear filtrate, was added 50 ml n-Heptane drop wise in 30 minutes at 40-45° C.
f) Slowly cool the reaction mixture to 10-15° C. and maintain this mixture at same temperature for about 2 hours.
g) Filter the separated solid and washed with 4 mL n-Heptane (Chilled).
h) Dry the material at below 40° C. under vacuum for 12 hours
Yield=1.45 g
Chromatographic purity (By HPLC)=99.91%
Water content=~4.24% w/w (by KF Coulometric titration)
XRPD as per FIG. 1; DSC as per FIG. 2; IR spectra as per FIG. 3 and Raman Spectra as per FIG. 4. The above mentioned examples, which are provided by way of illustration, should not be construed as limiting the scope of the invention with respect to parameter/s, ingredient/s and quantities used in any manner.

We claim:
1. A process for preparing Bortezomib (Ia) crystalline Form-SB

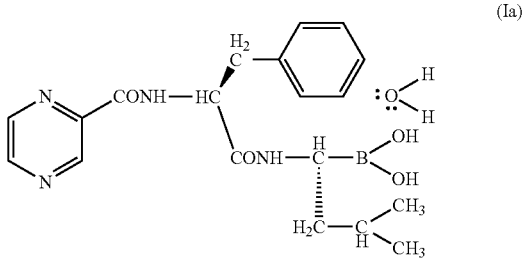

characterized by X-ray powder diffraction pattern comprising the characteristic 2θ° peaks of 5.6, 7.5, 9.8, 10.2, 11.3, 15.1, 18.0, 20.5, 21.5 and 23.6±0.20 2θ°, wherein peaks at 9.8 and 11.39±0.20 2θ° are un-split and 100% intensity peak is present at 5.6+0.20 2θ°, DSC isotherm comprising the endothermic peaks ranging between 45 to 60° C. (Peak-1) and 175 to 185° C. (Peak-2) and IR absorption characteristic peaks approximately at 3387 cm$^{-1}$, 3304 cm$^{-1}$, 2953 cm$^{-1}$, 2927 cm$^{-1}$, 2868 cm$^{-1}$, 1627 cm$^{-1}$, 1455 cm$^{-1}$, 1400 cm$^{-1}$, 1201 cm$^{-1}$, 1150 cm$^{-1}$, 1020 cm$^{-1}$, 747 cm$^{-1}$ and 702 cm$^{-1}$ and Raman absorption having characteristic peaks approximately at 3066 cm$^{-1}$, 1583 cm$^{-1}$, 1528 cm$^{-1}$, 1281 cm$^{-1}$, 1213 cm$^{-1}$, 1035 cm$^{-1}$, 1022 cm$^{-1}$ and 1004 cm$^{-1}$ comprising the steps of—
a) combining the Bortezomib with an aliphatic ester solvent or a mixture of aliphatic ester solvent and water;
b) raise the temperature up to about 40-70° C.;
c) stir the solution at same temperature up to a time between 15 to 60 minutes;
d) combine with aliphatic C6 to C7 hydrocarbon solvent;
e) optionally maintain the mixture for 10-60 minutes;
f) cooling the mixture up to about 10-40° C.; and
g) isolating the crystalline material.

2. A process for preparing Bortezomib (Ia) crystalline Form-SB according to claim 1, wherein aliphatic ester solvent is selected from C3 to C8 aliphatic ester solvent.

3. A process for preparing Bortezomib (Ia) crystalline Form-SB according to claim 1, wherein mixture of aliphatic ester solvent and water is having ratio between 90:10 to 99:1 v/v.

4. Bortezomib (Ia) as monohydrate crystalline Form-SB characterized by having water content of 3.5-6% w/w; X-ray powder diffraction pattern comprising characteristic 2θ° peaks selected from the XRPD peak set of 5.6, 7.5, 9.8, 10.2, 11.3, 15.1, 18.0, 20.5, 21.5 and 23.6±0.20 2θ°, wherein peaks at 9.8 and 11.39±0.20 2θ° are un-split and 100% intensity peak is present at 5.6±0.20 2θ°.

5. Bortezomib (Ia) according to claim 4, which is further characterized by DSC isotherm comprising two endothermic peaks ranging between—
a) Peak-1-Between 45 to 60° C.
b) Peak-2-Between 175-185° C.

6. Bortezomib (Ia) according to claim 4, further characterized by an IR absorption spectrum having characteristic peaks expressed in cm$^{-1}$ at approximately 3387 cm$^{-1}$, 3304 cm$^{-1}$, 2953 cm$^{-1}$, 2927 cm$^{-1}$, 2868 cm$^{-1}$, 1627 cm$^{-1}$, 1455 cm$^{-1}$, 1400 cm$^{-1}$, 1201 cm$^{-1}$, 1150 cm$^{-1}$, 1020 cm$^{-1}$, 747 cm$^{-1}$ and 702 cm$^{-1}$.

7. Bortezomib (Ia) according to claim 4, characterized by a Raman absorption spectrum having characteristic peaks expressed in cm$^{-1}$ at approximately 3066 cm$^{-1}$, 1583 cm$^{-1}$, 1528 cm$^{-1}$, 1281 cm$^{-1}$, 1213 cm$^{-1}$, 1035 cm$^{-1}$, 1022 cm$^{-1}$ and 1004 cm$^{-1}$.

8. Bortezomib (Ia) crystalline Form-SB characterized by X-ray powder diffraction pattern comprising the characteristic 2θ° peaks of 5.6, 7.5, 9.8, 10.2, 11.3, 15.1, 18.0, 20.5, 21.5 and 23.6±0.20 2θ°, wherein peaks at 9.8 and 11.39±0.20 2θ° are un-split and 100% intensity peak is present at 5.6±0.20 2θ°, DSC isotherm comprising the endothermic peaks ranging between 45 to 60° C. (Peak-1) and 175 to 185° C. (Peak-2) and IR absorption characteristic peaks at approximately 3387 cm$^{-1}$, 3304 cm$^{-1}$, 2953 cm$^{-1}$, 2927 cm$^{-1}$, 2868 cm$^{-1}$, 1627 cm$^{-1}$, 1455 cm$^{-1}$, 1400 cm$^{-1}$, 1201 cm$^{-1}$, 1150 cm$^{-1}$, 1020 cm$^{-1}$, 747 cm$^{-1}$ and 702 cm$^{-1}$.

9. Bortezomib (Ia) crystalline Form-SB according to claim 8, characterized by X-ray powder diffraction pattern substantially according to FIG. 1, DSC isothermal pattern substantially according to FIG. 2, IR absorption spectrum substantially according to FIG. 3 and Raman spectrum substantially according to FIG. 4.

10. Bortezomib (Ia) crystalline Form-SB according to claim 8 having water content in the range between 3.5-6.0% w/w.

* * * * *